(12) United States Patent
Aoki et al.

(10) Patent No.: US 9,576,500 B2
(45) Date of Patent: Feb. 21, 2017

(54) TRAINING SUPPORTING APPARATUS AND SYSTEM FOR SUPPORTING TRAINING OF WALKING AND/OR RUNNING

(71) Applicant: CASIO COMPUTER CO., LTD., Shibuya-ku, Tokyo (JP)

(72) Inventors: Nobuhiro Aoki, Kokubunji (JP); Yoshiharu Houjou, Tokyo (JP); Kazuko Hayashi, Hamura (JP); Koji Yamamoto, Fussa (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 344 days.

(21) Appl. No.: 14/494,227

(22) Filed: Sep. 23, 2014

(65) Prior Publication Data

US 2015/0120022 A1   Apr. 30, 2015

(30) Foreign Application Priority Data

Oct. 31, 2013 (JP) .................................. 2013-227426

(51) Int. Cl.

| | |
|---|---|
| *A61B 5/024* | (2006.01) |
| *G01C 22/00* | (2006.01) |
| *G06K 9/00* | (2006.01) |
| *G09B 19/00* | (2006.01) |
| *G04G 21/02* | (2010.01) |
| *G04G 21/04* | (2013.01) |

(52) U.S. Cl.
CPC ........... *G09B 19/0038* (2013.01); *G04G 21/02* (2013.01); *G04G 21/04* (2013.01); *A61B 5/024* (2013.01); *G01C 22/00* (2013.01)

(58) Field of Classification Search
CPC ... A61B 5/4023; A61B 5/6807; A61B 5/1123; A61B 5/681; A61B 5/6824; G01C 22/006; A43B 3/0031; A63B 2220/40; G01P 3/00
USPC ....................................................... 340/573.7
See application file for complete search history.

(56) References Cited

U.S. PATENT DOCUMENTS

| | | | |
|---|---|---|---|
| 8,562,489 B2 | 10/2013 | Burton et al. | |
| 2006/0173578 A1* | 8/2006 | Takenaka ............. | B62D 57/032 700/245 |

(Continued)

FOREIGN PATENT DOCUMENTS

| | | |
|---|---|---|
| JP | 2011516210 A | 5/2011 |
| JP | 2012524640 A | 10/2012 |

(Continued)

*Primary Examiner* — Fekadeselassie Girma
(74) *Attorney, Agent, or Firm* — Holtz, Holtz & Volek PC

(57) ABSTRACT

A training supporting system has a training supporting apparatus and an exercise form analyzing apparatus, the both apparatuses being connected to each other through a communication network. The training supporting apparatus is worn on the arm of a user and measures acceleration rates of motion of the user's body where the apparatus is fitted on, at least in the three directions along X-, Y- and Z-axes, while the user is walking or running. Receiving the measured acceleration rates from the training supporting apparatus through the communication network, the exercise form analyzing apparatus analyzes an exercise form including balance between arm swing and foot landing, and sends back the analysis result of the exercise form to the training supporting apparatus through the communication network.

13 Claims, 9 Drawing Sheets

(56) References Cited

U.S. PATENT DOCUMENTS

| | | | |
|---|---|---|---|
| 2006/0247800 A1* | 11/2006 | Takenaka | B62D 57/032 700/54 |
| 2007/0156283 A1* | 7/2007 | Takenaka | B62D 57/032 700/245 |
| 2008/0146968 A1* | 6/2008 | Hanawaka | A61B 5/1038 600/595 |
| 2009/0258710 A1 | 10/2009 | Quatrochi et al. | |
| 2010/0261526 A1* | 10/2010 | Anderson | G06F 3/016 463/31 |
| 2010/0331145 A1 | 12/2010 | Lakovic et al. | |
| 2011/0007468 A1 | 1/2011 | Burton et al. | |
| 2011/0032105 A1 | 2/2011 | Hoffman et al. | |
| 2011/0208444 A1* | 8/2011 | Solinsky | A61B 5/112 702/41 |
| 2011/0264264 A1* | 10/2011 | Shirokura | B62D 57/032 700/245 |
| 2012/0253234 A1* | 10/2012 | Yang | A61B 5/1038 600/595 |
| 2013/0245987 A1* | 9/2013 | Izumida | G01P 15/18 702/141 |
| 2014/0188257 A1* | 7/2014 | Ura | A63B 71/06 700/91 |
| 2014/0228985 A1* | 8/2014 | Elliott | A63B 71/06 700/91 |
| 2014/0288681 A1* | 9/2014 | Watanabe | A61B 5/6828 700/91 |
| 2014/0375461 A1* | 12/2014 | Richardson | G08B 21/0446 340/573.7 |
| 2015/0081061 A1* | 3/2015 | Aibara | A61B 5/1122 700/91 |
| 2016/0095539 A1* | 4/2016 | Kim | G01P 3/00 702/19 |
| 2016/0287937 A1* | 10/2016 | Fitzgerald | A63B 24/0062 |

FOREIGN PATENT DOCUMENTS

| | | |
|---|---|---|
| JP | 2013143996 A | 7/2013 |
| WO | 2009126818 A2 | 10/2009 |
| WO | 2010126825 A1 | 11/2010 |

* cited by examiner

TRAINING SUPPORTING APPARATUS AND SYSTEM FOR SUPPORTING TRAINING OF WALKING AND/OR RUNNING

CROSS-REFERENCE TO RELATED APPLICATION

The present application is based upon and claims the benefit of priority from the prior Japanese Patent Application No. 2013-227426, filed Oct. 31, 2013, the entire contents of which are incorporated herein by reference.

BACKGROUND OF THE INVENTION

1. Field of the Invention

The present invention relates to a training supporting apparatus and system which can analyze exercise form of a user, while the user wears the training supporting apparatus on the body and is walking or running.

2. Description of the Related Art

Up to now, a smartphone provided with an acceleration sensor is often used to obtain data representing a posture of a user, while he/she wears the smartphone on his/her own waist or other part of the body and is walking or running.

But wearing the smartphone on the body requires not only a very troublesome operation but also an accurate form analysis could not made to precisely evaluate motion such as arm swing. Therefore, a training supporting system has been expected, which releases the user from the troublesome operation of wearing a device on the body and can analyze an accurate motion such as arm swing.

Japanese Unexamined Patent Application Publication No. 2012-524640 and NO. 2011-516210 propose technologies concerning modules provided with a wrist band for monitoring athletic performance given by a user. Further, a technology is disclosed in Japanese Unexamined Patent Application Publication No. 2013-143996, which uses an exercise measuring apparatus of a wrist-band type, provided with an acceleration sensor, and measure arm swing of a user while the user is running.

Using the technologies disclosed in Japanese Unexamined Patent Application Publication No. 2012-524640 and NO. 2011-516210, the users will be released from the troublesome operation of wearing an device on the body but cannot make an advanced performance evaluation such as form analysis. Further, in accordance with the technology disclosed by Japanese Unexamined Patent Application Publication No. 2013-143996, the users can analyze an exercise form such as arm swing, by using a large-scale motion capture system but cannot evaluate accurate balance between arm swing and foot landing. The technology has a limitation in the analyzing function.

The present invention will provide a training or exercise supporting apparatus and system which can analyze balance in form while the user wears on the wrist and is walking or running.

SUMMARY OF THE INVENTION

According to one aspect of the invention, there is provided a training supporting apparatus connected through a communication network with an exercise form analyzing apparatus, wherein the exercise form analyzing apparatus analyzes an exercise form while a user is walking or running, the training supporting apparatus which comprises a measuring unit which is worn on the arm or the wrist of the user and measures acceleration rates at least in the three directions along X-, Y- and Z-axes, while the user is walking or running, a sending unit for sending information of the acceleration rates measured by the measuring unit to the exercise form analyzing apparatus through the communication network, a receiving unit for receiving through the communication network an analysis result made by the exercise form analyzing apparatus, including balance between arm swing and foot landing, an output unit for outputting the analysis result received by the receiving unit, and a controlling unit for controlling said sending unit, said receiving unit, and said output unit.

According to another aspect of the invention, there is provided an exercise form analyzing apparatus connected to a training supporting apparatus through a communication network, wherein the training supporting apparatus is worn on the arm or the wrist of a user and measures acceleration components of motion of the user's body where said training supporting apparatus is fitted on, at least in the three directions along X-, Y- and Z-axes, while the user is walking or running, the exercise form analyzing apparatus which comprises a controlling unit which analyzes an exercise form including balance between arm swing and foot landing, based on the acceleration components received from the training supporting apparatus through the communication network, and sends an analysis result of the exercise form to the training supporting apparatus through the communication network.

According to other aspect of the invention, there is provided a training supporting method in a training supporting apparatus connected to an exercise form analyzing apparatus through a communication network, wherein the training supporting apparatus is worn on the arm of a user and measures acceleration rates of motion of the user's body where said training supporting apparatus is fitted on, at least in the three directions along X-, Y- and Z-axes, while the user is walking or running, the method which comprises a sending step of sending information of the measured acceleration rates to the exercise form analyzing apparatus through the communication network, a receiving step of receiving through the communication network an analysis result including balance between arm swing and foot landing from the exercise form analyzing apparatus, an outputting step of outputting the received analysis result, and a displaying step of displaying said analysis result.

According to still another aspect of the invention, there is provided an exercise form analyzing method in an exercise form analyzing apparatus connected to a training supporting apparatus through a communication network, wherein the training supporting apparatus is worn on the arm or the wrist of a user, and has a measuring unit for measuring acceleration rates of motion of the user's body where said training supporting apparatus is fitted on, at least in the three directions along X-, Y- and Z-axes, while the user is walking or running, the exercise form analyzing method which comprises a receiving step of receiving the acceleration rates from the training supporting apparatus through the communication network, an analyzing step of analyzing an exercise form including balance between arm swing and foot landing, based on the received acceleration rates, and a sending step of sending an analysis result of the exercise form to the training supporting apparatus through the communication network.

According to still other aspect of the invention, there is provided a training supporting system which comprises a training supporting apparatus and an exercise form analyzing apparatus, both apparatuses being connected to each other through a communication network, wherein the training supporting apparatus comprises a measuring unit which is worn on the arm or the wrist of a user and measures acceleration rates of motion of the user's body where said training supporting apparatus is fitted on, at least in the three directions along X-, Y- and Z-axes, while the user is walking or running, and a controlling unit which receives an analysis result including balance between arm swing and foot landing from the exercise form analyzing apparatus through the communication network, and outputs the received analysis result, and the exercise form analyzing apparatus analyzes an exercise form including balance between arm swing and foot landing, based on the acceleration rates received from the training supporting apparatus through the communication network, and sends the analysis result of the exercise form to the training supporting apparatus through the communication network.

According to yet other aspect of the invention, there is provided a training supporting apparatus which comprises a measuring unit which is worn on the arm or the wrist of a user and measures acceleration components of motion of the user's body where said measuring unit is fitted on, at least in the three directions along X-, Y- and Z-axes, while the user is walking or running, and a controlling unit which divides the acceleration components output from the measuring unit into acceleration components at least for one step on the basis of the acceleration components at the foot landing, compares waveforms of the divided acceleration components with waveforms of previously registered acceleration components, extracts acceleration components of arm swing at the time of foot landing from the acceleration components successively output from the measuring unit to analyze balance in timing between arm swing and foot landing while the user is walking or running, and outputs the analyzed balance in timing between arm swing and foot landing.

According to still other aspect of the invention, there is provided a training supporting method in a training supporting apparatus which is worn on the arm of a user and measures acceleration rates of motion of the user's body where said training supporting apparatus is fitted on, at least in the three directions along X-, Y- and Z-axes, while the user is walking or running, the method which comprises a dividing step of dividing the acceleration rates of motion of the user's body where said training supporting apparatus is fitted on into acceleration rates at least for one step on the basis of the acceleration rates at a shock of foot landing, a comparing step of comparing waveforms of the divided acceleration rates with waveforms of previously registered acceleration rates, an extracting step of extracting acceleration rates of arm swing at the time of foot landing from the acceleration rates successively output from the training supporting apparatus, when it is determined that the compared waveforms do not coincide to each other, thereby analyzing balance in timing between arm swing and foot landing while the user is walking or running, and an outputting step of outputting the analyzed balance in timing between arm swing and foot landing.

DETAILED DESCRIPTION OF THE PREFERRED EMBODIMENTS

Figure 1:
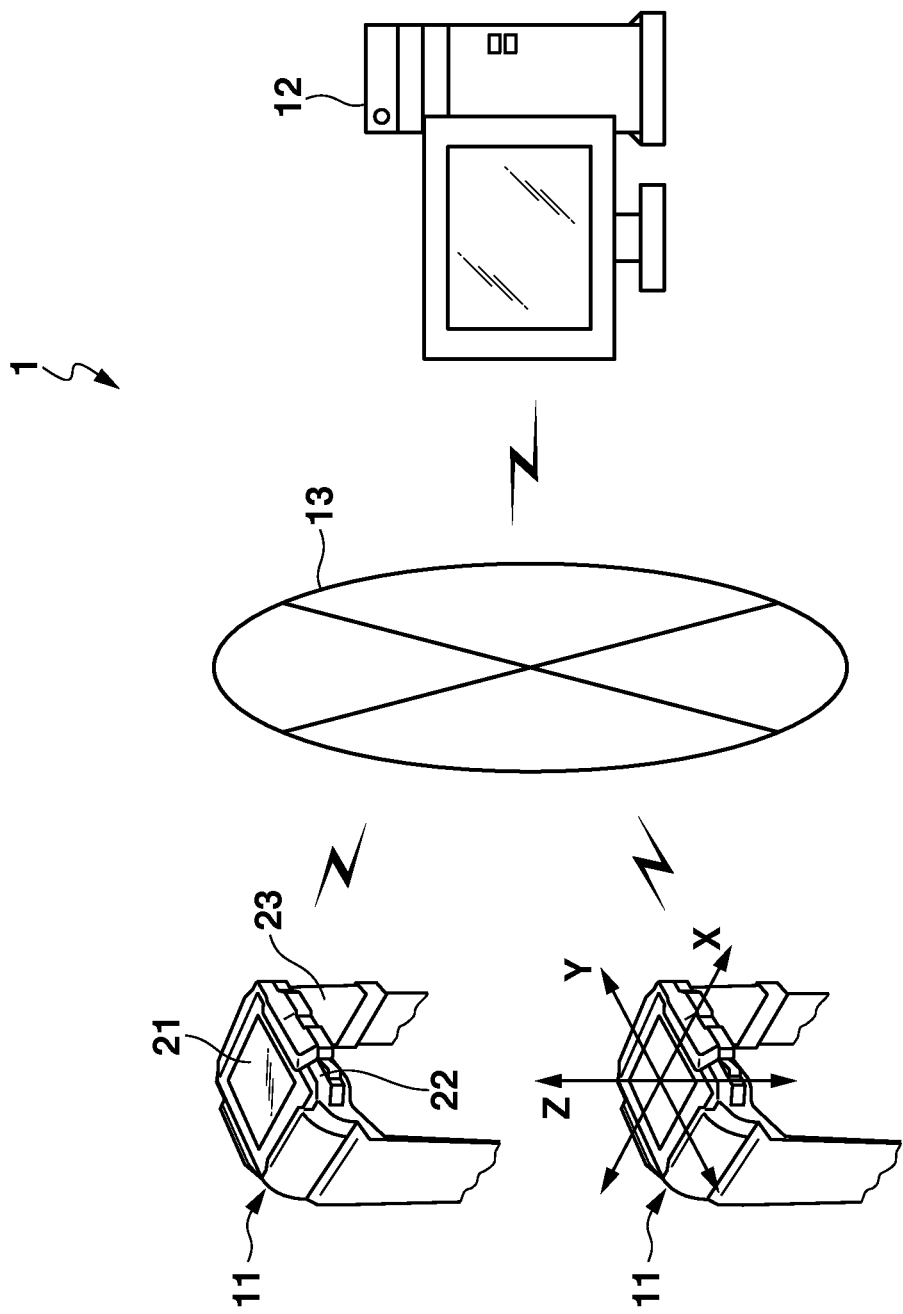
FIG. 1 is a view illustrating a training supporting system according to the embodiment of the present invention.

The embodiments of the present invention will be described with reference to the accompanying drawings in detail. Throughout the whole description of the embodiments of the present invention, like elements are designated by like reference numerals.

Configuration of Training Supporting System

FIG. 1 is a view illustrating the training supporting system 1 according to the embodiment of the invention. As shown in FIG. 1, the training supporting system 1 comprises a training supporting apparatus 11, an exercise form analyzing apparatus 12, and a communication network 13 such as an IP (Internet Protocol) network, through which the training supporting apparatus 11 and the exercise form analyzing apparatus 12 are connected to each other. For convenience in the following description, the training supporting apparatus 11 will be referred to as a "wrist terminal" 11, and the exercise form analyzing apparatus 12 will be referred to as an "exercise form analyzing server" 12. If the wrist terminal 11 has a built-in short distance wireless communication function, a smartphone (not shown) can be used to communicate with the exercise form analyzing apparatus 12.

In the training supporting system 1 shown in FIG. 1, while a user wears the wrist terminal 11 on his or her wrist and is walking or running (jogging), said wrist terminal 11 measures acceleration components (waveforms) of motion of the user's wrist, that is, a part of the user's body where said wrist terminal 11 is worn on, at least in the three axial directions along X-, Y-, and Z-axes, and meanwhile the exercise form analyzing server 12 analyzes an exercise form including balance between arm swing and foot landing, based on the acceleration components supplied from the wrist terminal 11 through the communication network 13, and sends back through the communication network 13 to the wrist terminal 11 the analysis result or the analyzed exercise form. Receiving the analysis result or the analyzed exercise form from the exercise form analyzing server 12, the wrist terminal 11 displays the analyzed exercise form, for example, as shown in FIG. 10 (*a*) to FIG. 10 (*c*). The detail will be described later. The balance means relationships between plural pieces of data.

The wrist terminal 11 is provided with a wristband 23 to be wrapped around the wrist of the user for putting the wrist terminal 11 on the user's wrist while the user is walking or running (jogging), and has an external appearance like a wristwatch having a displaying unit covered with a glass surface 21 and a rear cover 22. The wrist terminal 11 has a built-in acceleration sensor for detecting acceleration components of motion of a part (hereinafter, referred to as the "fitting part") of the user's body where said wrist terminal 11 is worn on at least in the three axial directions of the X-, Y-, and Z-axes. The X-axis corresponds to the elongated direction along the user's arm where said wrist terminal 11 is worn on, and the Y-axis corresponds to the direction which crosses with the elongated direction at right angles. The Z-axis corresponds to the vertical direction from the glass surface 21 of the wrist terminal 11 to the rear cover 22 or vice versa. For convenience, in the following description, the direction along X-axis toward the wrist will be referred to as the "forward direction" (the reverse direction will be referred to as the "backward direction"), and the direction along Z-axis toward the rear cover 22 will be referred to as the "downward direction" (the reverse direction will be referred to as the "upward direction").

Configuration of Wrist Terminal

Figure 2:
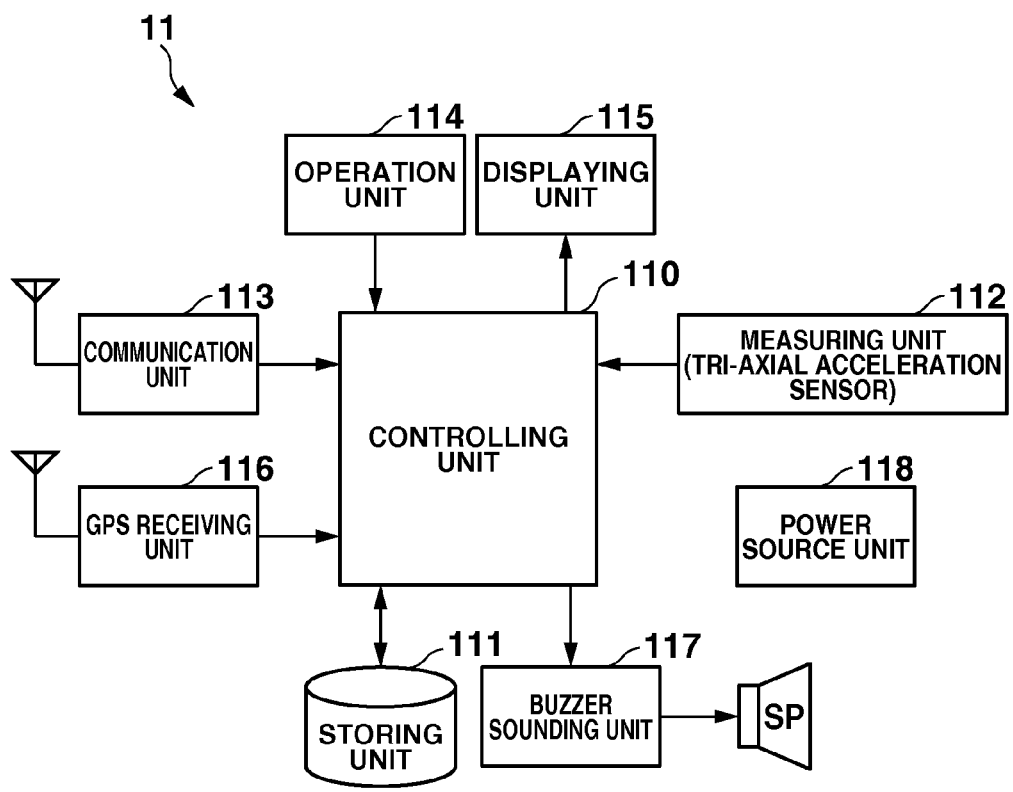
FIG. 2 is a block diagram of a configuration of a training supporting apparatus (wrist terminal) in the training supporting system according to the embodiment of the invention.

The wrist terminal 11 is connected through the IP network 13 with the exercise form analyzing server 12 for analyzing the user's exercise form while the user is walking or running (jogging). FIG. 2 is a block diagram of a configuration of the wrist terminal 11. As shown in FIG. 2, the wrist terminal 11 comprises a controlling unit 110, a storing unit 111, a measuring unit 112, a communication unit 113, an operation unit 114, a displaying unit 115, GPS (Global Positioning System) receiving unit 116, a buzzer sounding unit 117, and a power source unit 118.

The controlling unit 110 is provided with a micro-processor, which successively reads and runs a program (terminal program) stored in the storing unit 111 to communicate with the exercise form analyzing server 12 through the communication unit 113 and the IP network 13. While the user is walking or running, the measuring unit 112 measures acceleration data of the fitting part, that is, the user's body where the wrist terminal 11 is worn on, at least in the three directions along the X-, Y-, and Z-axes, and the controlling unit 110 sends the acceleration data measured by the measuring unit 112 to the exercise form analyzing server 12, requesting for exercise form analyzing. Receiving the request of analyzing an exercise form, the exercise form analyzing server 12 analyzes the exercise form of the user, and the controlling unit 110 receives the analysis result or the analyzed exercise form from the exercise form analyzing server 12 and outputs the analyzed exercise form to the displaying unit 115 or to the buzzer sounding unit 117, or to the both.

The storing unit 111 is a semi-conductor storing device having DRAM (Dynamic Random Access Memory) and/or SDRAM (Synchronous DRAM) as a storing element or a magnetic disk device such as a hard disk drive. In addition to a program area for storing the program of the present embodiment, the storing unit 111 has an area for storing data generated while the controlling unit 110 is running the program and exercise form-analyzing data obtained by the form analyzing server 12 including balance between arm swing and foot landing.

The measuring unit 112 has a built-in tri-axial acceleration sensor. The tri-axial acceleration sensor is a sort of sensors and consists of one device of MEMS (Micro Electro Mechanical System) which is capable of measuring acceleration rates in three directions of the X-, Y-, and Z-axes. In the present embodiment of the invention, a semi-conductor type sensor most circulate in the market is used as the tri-axial acceleration sensor. In addition to the semi-conductor type sensors, electrostatic capacitance type sensors, piezo-resistance acceleration sensors, and heat detection type sensors can be employed in the embodiment.

The communication unit 113 serves as a communication interface for communication with the IP network 13. For instance, the communication unit 113 communicates with the exercise form analyzing server 12 in accordance with TCP/IP (Transmission Control Protocol/Internet Protocol). The communication unit 113 sends the exercise form analyzing server 12 measurement data measured by the measuring unit 112 and generated by the controlling unit 110, and receives through the IP network 13 the resultant form-analyzing data generated by the exercise form analyzing server 12 and transfers the received data to the controlling unit 110.

The operation unit 114 is an input device such as a key switch, or a pointing device such as a mouse. When operated by the user, the operation unit 114 generates an event of instructing the controlling unit 110 to start measurement. The displaying unit 115 is a displaying monitor comprising a displaying element such as an LCD (Liquid Crystal Device) and/or an Organic EL (Organic Electronic-Luminescense) and a driver circuit for driving the displaying element. The displaying unit 115 displays images generated by the controlling unit 110, for example, such as those shown in FIG. 10(*a*) to FIG. 10(*c*). The operation unit 114 and the displaying unit 115 can be replaced with a touch panel having the input function of the operation unit 114 and the displaying function of the displaying unit 115.

The GPS receiving unit 116 uses GPS satellites to measure the current position of the user who wears the wrist terminal 11. More specifically, receiving electromagnetic waves from GPS satellites through an antenna (not shown), the GPS receiving unit 116 obtains position data including a latitude and a longitude, indicating the current position of the user, and outputs the obtained position data to the controlling unit 110.

The buzzer sounding unit 117 outputs audio data generated by the controlling unit 110 to a speaker SP. The buzzer sounding unit 117 outputs a message generated by the controlling unit 110 as an alarm, buzzer and/or voice. The power source unit 118 is a battery, which supplies power to the hardware blocks consisting the wrist terminal 11 such as the controlling unit 110, storing unit 111, measuring unit 112, communication unit 113, operation unit 114, displaying unit 115, GPS receiving unit 116, and buzzer sounding unit 117.

Configuration of Exercise Form Analyzing Server

Figure 3:
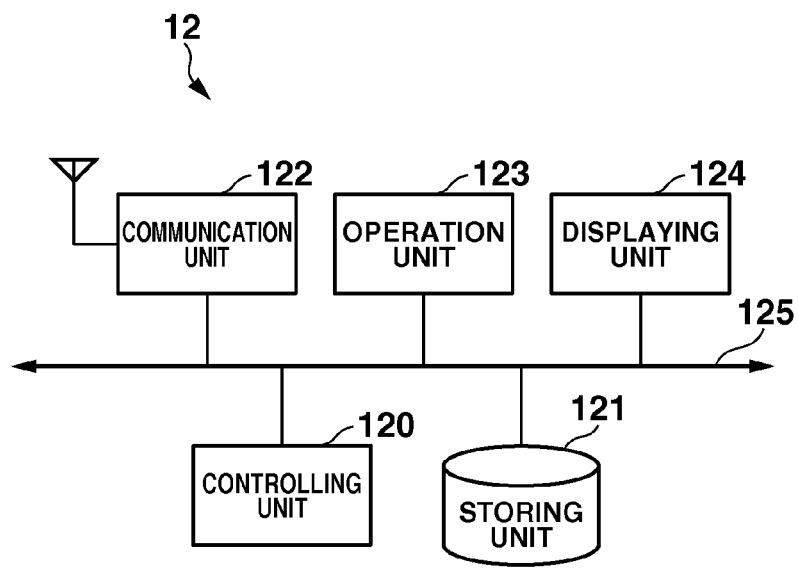
FIG. 3 is a block diagram of a configuration of an exercise form analyzing apparatus (exercise form analyzing server) in the training supporting system according to the embodiment of the invention.

The exercise form analyzing server 12 is connected through the IP network 13 with the wrist terminal 11 which is put on the arm of the user to measure acceleration components of motion of the user's arm at least in the directions of X-, Y-, and Z-axes. FIG. 3 is a block diagram of a configuration of the exercise form analyzing server 12.

As shown in FIG. 3, the form analyzing server 12 comprises a controlling unit 120, a storing unit 121, a communication unit 122, an operation unit 123, a displaying unit 124, and a system bus 125 consisting of plural lines for dresses, data, and control. These units are connected with each other through the system bus 125.

The controlling unit 120 is provided with a micro-processor, which successively reads and runs a program (server program) stored in the storing unit 121 to communicate with the wrist terminal 11 through the communication unit 122 and the IP network 13. Receiving from the wrist terminal 11 through the IP network 13 data of the acceleration components of motion of the fitting part (or the user's body where the wrist terminal 11 is worn on) in the three directions, the controlling unit 120 analyzes an exercise form (including balance between arm swing and foot landing) of the user based on the received data, and sends through the IP network 13 the analysis result to the wrist terminal 11 which has made request for sending back the analysis result.

Receiving from the wrist terminal 11 the data of the tri-axial acceleration components of motion of the fitting part (or the user's body where the wrist terminal 11 is worn on), it is also possible for the controlling unit 120 to detect variation in balance between the acceleration components in X- and Y-axes at foot landing, and to analyze a timing balance between arm swing in the upper half of the body and foot landing. Receiving from the wrist terminal 11 through the IP network 13 the data of the tri-axial acceleration components of motion of the fitting part, (that is, the user's body where the wrist terminal 11 is worn on) it is possible for the controlling unit 120 to sample the received data at a given interval to delete sampled data which includes the acceleration component in X-axis showing almost zero, the acceleration component in Y-axis increasing greater than the last sampled one, and the acceleration components in Y- and Z-axes increasing in the predetermined directions at a shock of foot landing, from the data to be subjected to analysis of balance between arm swing and foot landing.

The storing unit 121 is a semi-conductor storing device having DRAM and/or SDRAM as a storing element or a magnetic disk device such as a hard disk drive. In addition to a program area for storing a program (server program) of the procedure shown in FIG. 6, the storing unit 121 has an area for storing (1) exercise form analyzing data (including balance between arm swing and foot landing) generated while the controlling unit 120 is executing the program, (2) registered exercise forms representing normal exercise forms at normal running and required to be referred to when the exercise form analysis is made, and (3) measurement data sent from the wrist terminal 11.

The communication unit 122 serves as a communication interface for communication with the IP network 13. For instance, the communication unit 122 communicates with the wrist terminal 11 in accordance with TCP/IP. The communication unit 122 receives from the wrist terminal 11 through the IP network 13 the measurement data of the fitting part, (that is, the user's body where the wrist terminal 11 is worn on) and transfers the received data to the controlling unit 120. Further, the communication unit 122 sends through the IP network 13 the wrist terminal 11 the exercise form analyzing data generated by the controlling unit 120.

The operation unit 123 is an input device such as a key switch, or a pointing device such as a mouse. The displaying unit 124 is a displaying monitor comprising a displaying element such as an LCD and/or an Organic EL and a driver circuit for driving the displaying element.

Operation of Training Supporting System

Figure 4A:
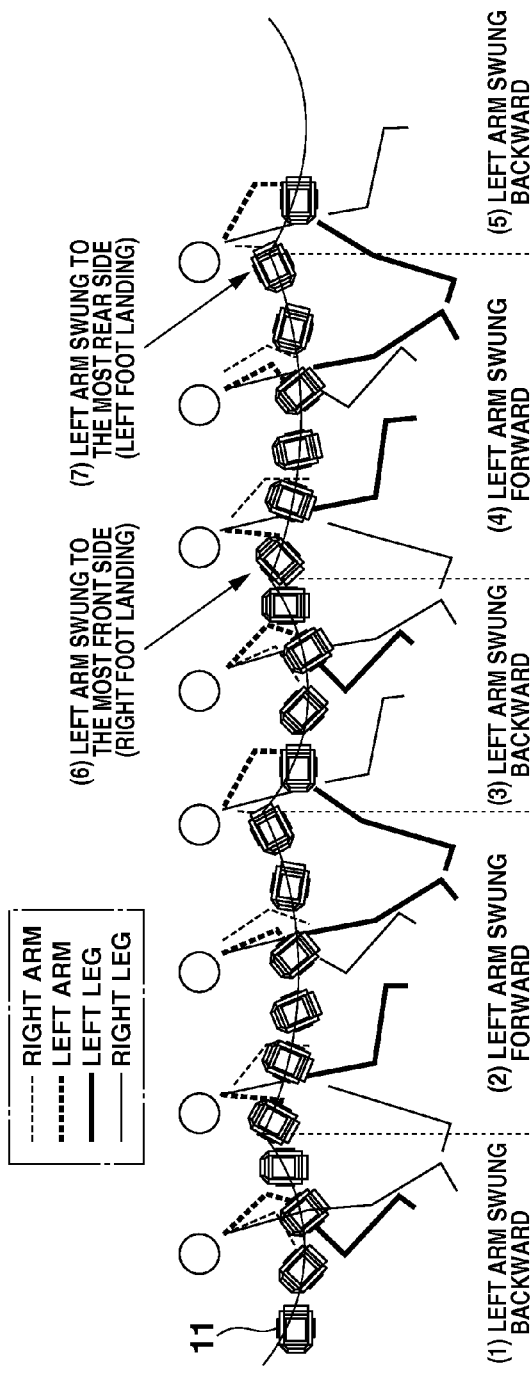
FIG. 4A is a view illustrating coordinated motion of the arms and legs of a user while the user wears the wrist terminal on his/her left wrist and is running.
Figure 4B:
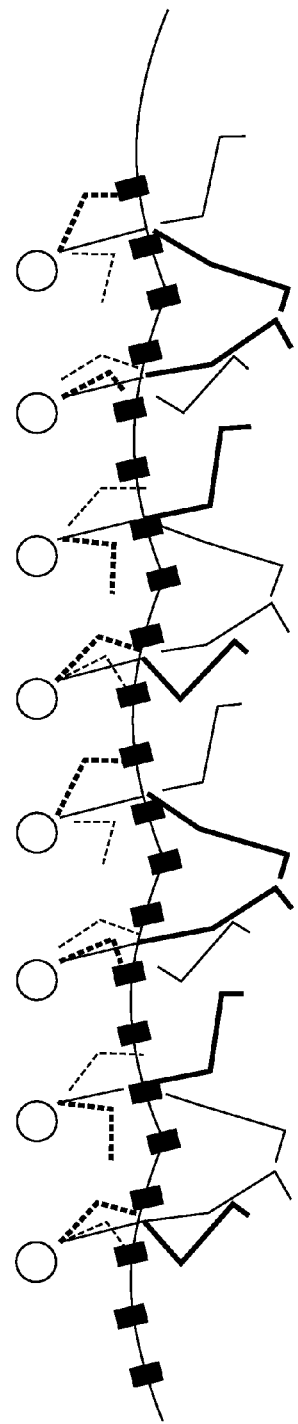
FIG. 4B is a view illustrating coordinated motion of the arms and legs of the user while the user wears a tri-axial acceleration sensor on his/her waist and is running.

At first, the running form and movement of the built-in tri-axial acceleration sensor of the measuring unit 112 of the wrist terminal 11 will be described with reference to FIG. 4A and FIG. 4B. FIG. 4A is a view illustrating coordinated motion of the arms and legs of the user while the user wears the wrist terminal 11 on his or her left wrist, and is running. FIG. 4B is a view illustrating coordinated motion of the arms and legs of the user while the user wears the tri-axial acceleration sensor on his or her waist and is running. In FIG. 4A and FIG. 4B, the motion of the left wrist is indicated by a bold dotted line, the motion of the right wrist is indicated by a fine dotted line, the motion of the left leg is indicated by a bold line, and the motion of the right leg is indicated by a fine line.

As illustrated in FIG. 4A, the user wearing the tri-axial acceleration sensor swings the left arm backward (swings the right arm forward) in conjunction with the forward motion of the left leg, and swings the left arm forward (swings the right arm backward) in conjunction with the forward motion of the right leg. A period within which the above motions of the arms and legs are executed is defined as one cycle. As shown in FIG. 4A, these motions are repeatedly executed (refer to (1) to (5)). A position where the wrist terminal 11 is held at the time when the right foot has landed and the left arm has been swung to the most front is indicated at a position (6) in FIG. 4A. A position where the wrist terminal 11 is held at the time when the left foot has landed and the left arm has been swung to the most rear side is indicated at a position (7) in FIG. 4A.

Figure 5:
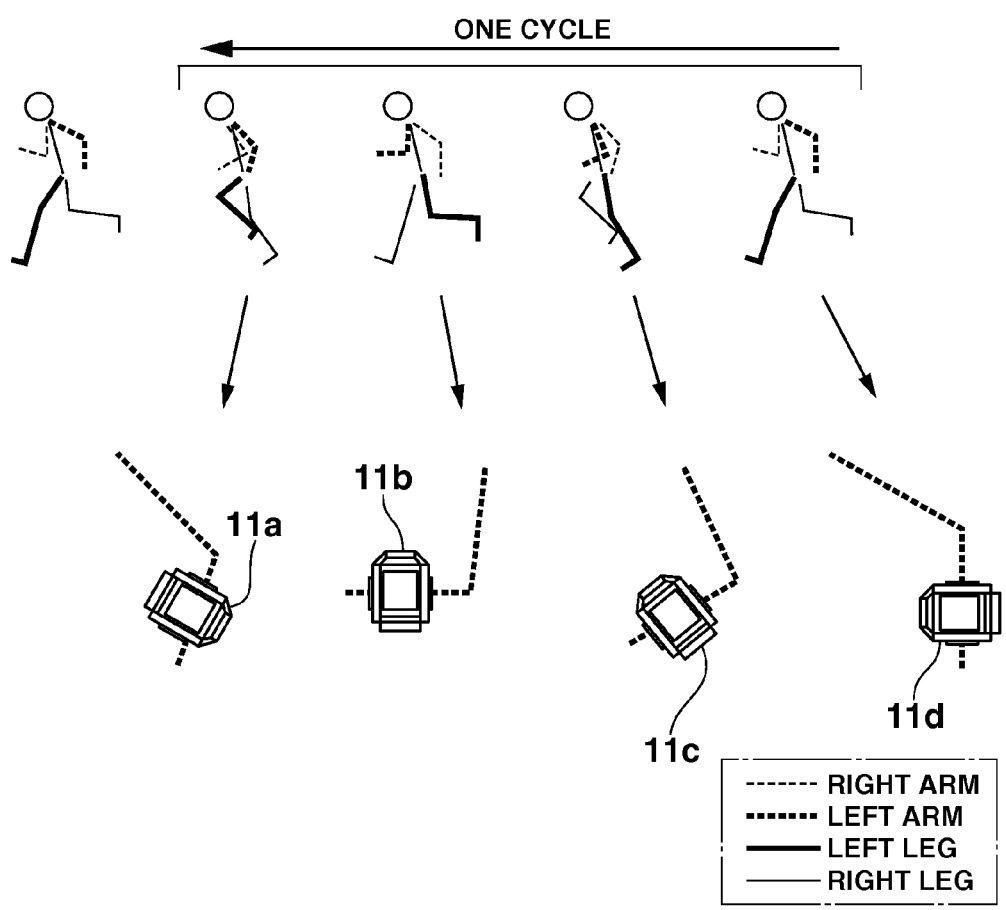
FIG. 5 is a view illustrating motions of the user wearing the wrist terminal within one cycle, including movement of the wrist terminal.

FIG. 5 is a view illustrating motion of the user wearing the wrist terminal 11 within one cycle, and movement of the wrist terminal 11. It is defined that the motion of "forward motion of the right leg and the following forward motion of the left leg" is performed within "one cycle" while the user is walking or running.

Figure 6:
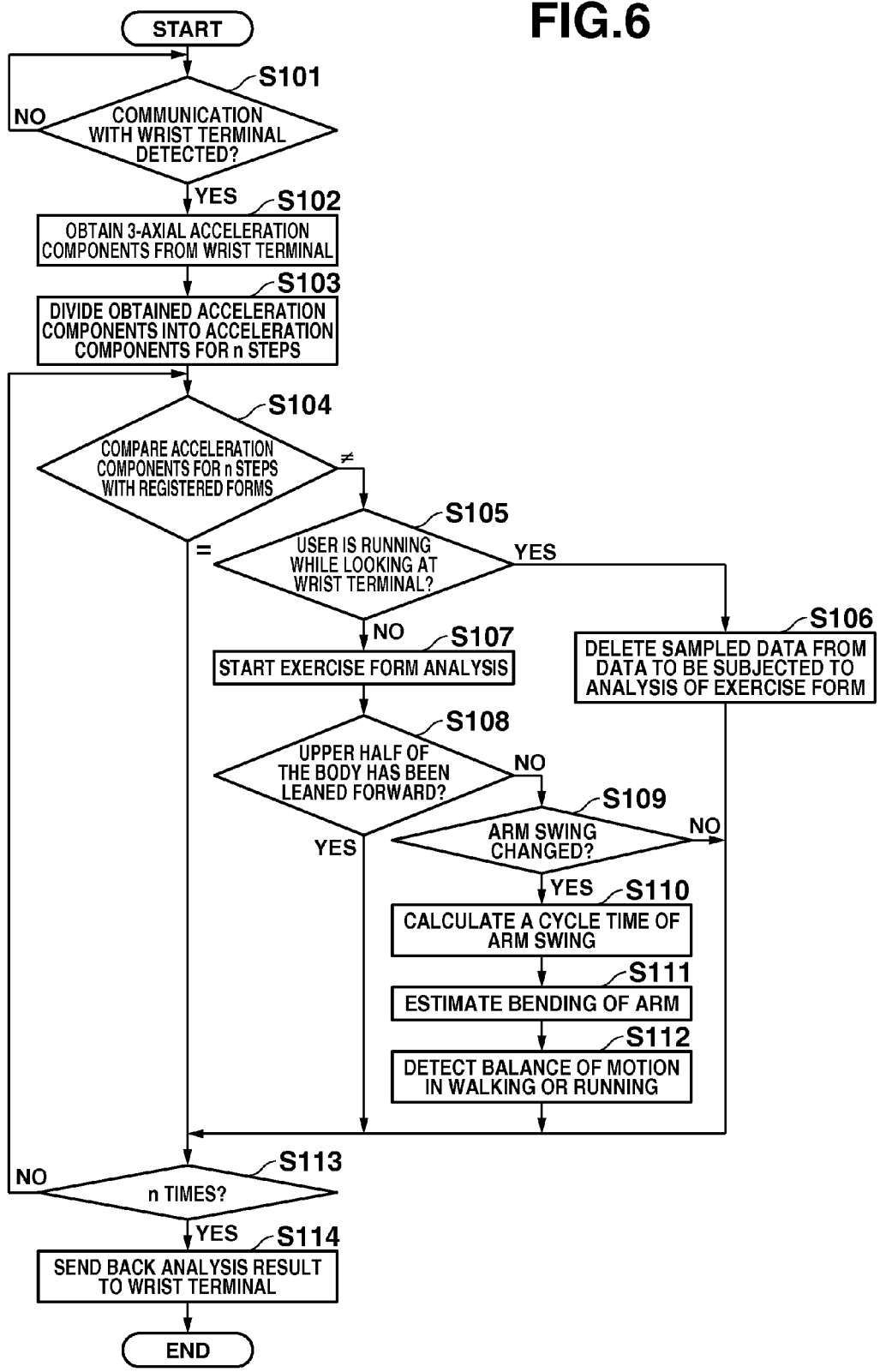
FIG. 6 is a flow chart of operation of the exercise form analyzing apparatus in the training supporting system according to the embodiment of the invention.

FIG. 6 is a flow chart of operation of the training supporting system according to the embodiment of the invention.

In FIG. 6, the exercise form analyzing server 12 (controlling unit 120) always keeps watching communication with the wrist terminal 11 (step S101). When the communication with the wrist watch 11 has been detected (YES at step S101), the exercise form analyzing server 12 (controlling unit 120) obtains the tri-axial acceleration components of motion of the fitting part (that is, the user's body where the wrist terminal 11 is worn on) from the wrist terminal 11 through the IP network 13 and the communication unit 122 (step S102).

The controlling unit 120 divides the obtained tri-axial acceleration components into data components for n-steps (one step or two steps) (step S103). To divide the acceleration components into acceleration components for n steps, the controlling unit 120 detects peak values of the tri-axial acceleration components, which means that the controlling unit 120 detects the greatest shock which will be given to the wrist terminal 11 at the time of the foot landings while the user is walking or running, thereby dividing the acceleration components.

Figure 7A:
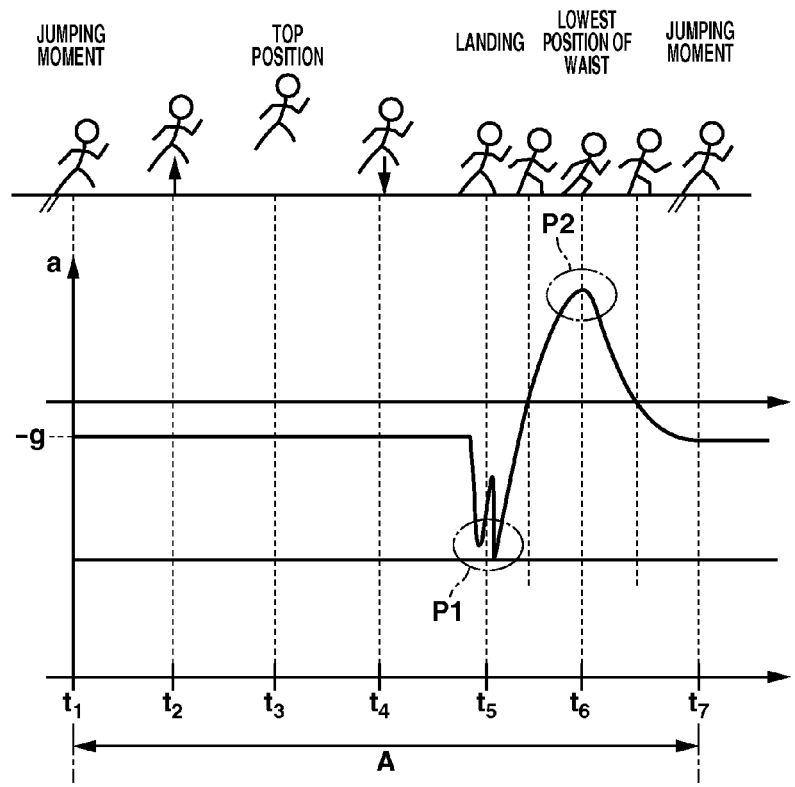
FIG. 7A is a view showing a relationship between movement of the user (runner) and an acceleration rate measured by a measuring unit of the training supporting apparatus (wrist terminal).

FIG. 7A is a view showing relationship between motion of the user (runner) and acceleration rates measured in the vertical direction by the measuring unit 112 of the wrist terminal 11. FIG. 7A is a view showing a time period "A" of one step of the runner, which has been obtained by experiment. As shown in FIG. 7A, the acceleration rate in the vertical direction shows the downward peak value P1 at a landing timing t5, and the upward peak value P2 at a timing t6 where the runner's waist is held lowest. This result will allow analysis of the landing cycle and calculation of landing timings.

Figure 7B:
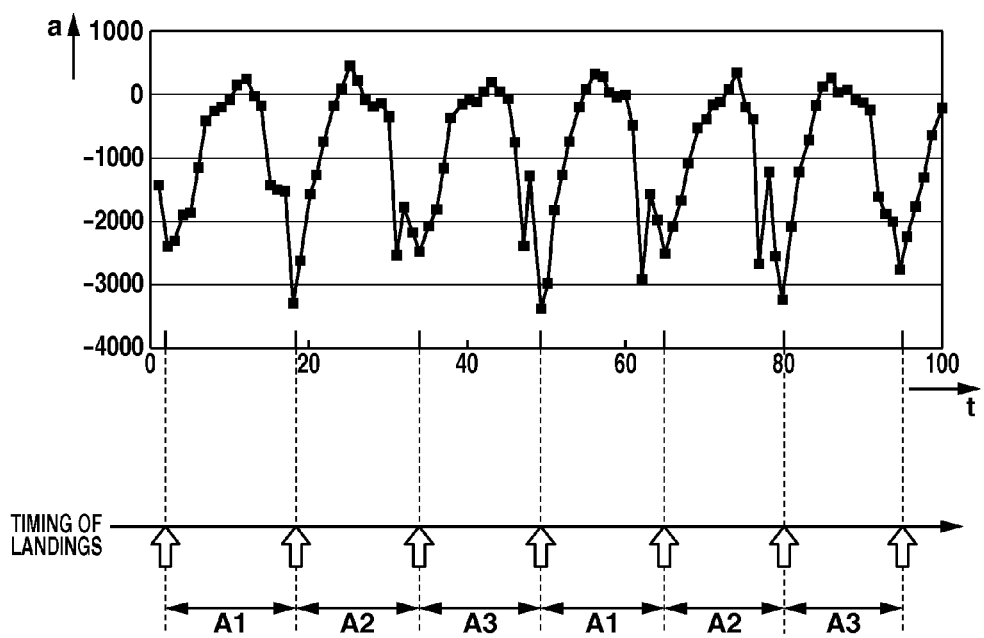
FIG. 7B is a graph indicating the acceleration rate plotted against time while the user is running.

FIG. 7B is a graph indicating acceleration rates plotted against times while the user is running. In FIG. 7B, reference symbols A1, A2, A3 each represent a time period equivalent to the time period "A" shown in FIG. 7A, which corresponds to a time period of one step taken by the runner. For instance, the landing timing t5 is specified in FIG. 7A to calculate one cycle. Then, the timing of the following foot landing is calculated, using an average of time periods of following continuous 10 steps.

Now, the description will return to the flow chart of FIG. 6. Receiving from the wrist terminal 11 the tri-axial acceleration data of the fitting part, the controlling unit 120 divides the received acceleration data into acceleration components for n steps and then compares the divided acceleration components for n steps with the walking or running forms, which are previously registered in a predetermined area of the storing unit 121 (step S104). In analyzing the motion of leg and arm in one cycle of walking or running, if the user keeps a right posture as well as right arm swing, while he/she is walking or running, the acceleration rates in the directions of X-, Y- and Z-axes output from the built-in tri-axial acceleration sensor (measuring unit 112) of the wrist terminal 11 will have substantially the same waveforms for every cycle. In the exercise form analyzing server 12 of the present embodiment, it is presumed that if the acceleration rates in the three directions have substantially the same waveforms for every cycle as described above, such acceleration rates are output when the user is walking or running in the normal exercise form.

If the user should break his/her normal exercise form, or when his/her walking or running form is compared with the registered exercise from for n steps and the both forms do not coincide with each other (NO or ≠ at step S104), then the controlling unit 120 will work as follows. When his/her walking or running forms do not coincide with the registered exercise forms (NO or ≠ at step S104), that is, when the user breaks his/her normal exercise form, it is estimated that the user is running, while looking at the wrist terminal 11. When the user has taken motion of looking at the wrist terminal 11, the wrist terminal 11 is brought before the user's face, and it is clear that the user does not take the right exercise form. Since the user is looking at the wrist terminal 11, even if the built-in tri-axial acceleration sensor (measuring unit 112) of the wrist terminal 11 has detected that the user is looking at the wrist terminal 11, it is necessary to delete the detected data from data to be subjected to analysis of exercise form.

As shown in FIG. 4A and/or in FIG. 5, when the user wears the wrist terminal 11 on his/her left wrist, and when the user runs while looking at the wrist terminal 11 (YES at step S105), the acceleration component in the direction of X-axis will be little, and the acceleration components in the directions of Y-, and Z-axes will increase. Further, at shock of foot landing, the acceleration component in the direction of Y-axis will increase forward and the acceleration component in the directions of Z-axis will increase downward. Therefore, when these changes in the acceleration components have been detected, the controlling unit 120 deletes these the acceleration components from the data to be subjected to analysis of exercise form (step S106). When the user is running with the face looking forward without looking at the wrist terminal 11 (NO at step S105), the exercise form analysis, that is, the running form analysis starts (step S107).

When the running form is analyzed, the controlling unit 120 judges whether the runner has leaned the upper half of the body forward (step S108). When the upper half of the body is leaned forward, the position of the wrist terminal 11 will change and the way of foot landing also will change accordingly. Therefore, since the acceleration rates in the directions of X-, Y- and Z-axes sent from the tri-axial acceleration sensor of the wrist terminal 11 will be different from data obtained while the user is running with the normal posture held, it will be easily determined (at step S108) whether the runner has leaned the upper half of the body forward. When the controlling unit 120 has determined that the upper half of the body is not leaned forward (NO at step S108), then the controlling unit 120 judges whether the user has changed arm swing (step S109).

When the user has changed arm swing (YES at step S109), and, for example, when the user's arm is swung sideways not back and forward, some change will be detected in the waveform of either one of the acceleration rates in the directions of X-, Y- and Z-axes output from the built-in acceleration sensor (measuring unit 112) of the wrist terminal 11, and therefore, it can easily be determined that the arm swing has changed. In the present embodiment, since the direction perpendicular to the glass surface 21 and the rear cover 22 of the wrist terminal 11 worn on the user's wrist is defined as Z-axis, if it is assumed that the wrist terminal 11 is worn on the back of the wrist and that the arm is straightly swung back and forward, the acceleration components will be generated substantially in the directions of X-, and Y-axes but the acceleration component will be detected little in the direction of Z-axis. If the arm is swung sideways, the acceleration component will increase in the direction of Z-axis.

Then, extracting the back and forward movement of the arm swing from the acceleration components in the directions of X-, Y- and Z-axes output from the acceleration sensor (measuring unit 112) of the wrist terminal 11, the controlling unit 120 calculates a cycle time of the arm swing (step S110) and estimates bending of the arm (arm-swing rate and arm bending angle) (step S111). In particular, the arm swing plays an important roll to produce a rhythm of walking or running. Since the acceleration components in the directions of X-, and Y-axes are repeated in the example shown in FIG. 5, the cycle time of the arm swing can be obtained by detecting a timing at which the substantially same waveform repeatedly appears. When the arm is bent too much, the wrist terminal 11 will be swung within a short range, and on the contrary, when the arm is not bent so much but rather kept straight, the wrist terminal 11 will be swung greatly. In this way, the amplitude of the arm swing can be calculated by analyzing the cycle time of the arm swing and the acceleration components of motion of the arm swing, whereby how much the arm is bent can be estimated.

Figure 8A:
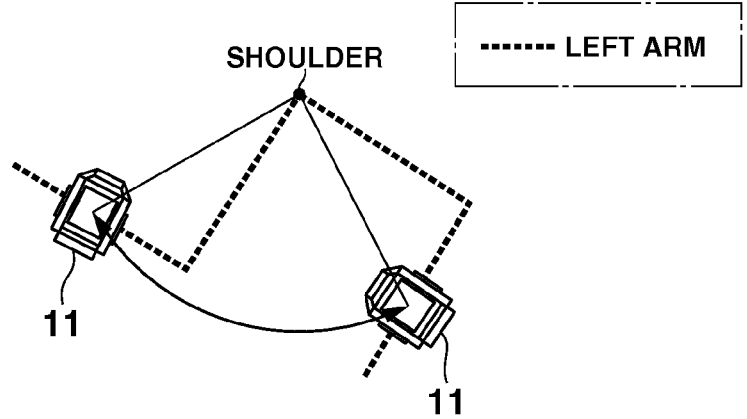
FIGS. 8A, 8B and 8C are views showing relationships between the movement of the training supporting apparatus (wrist terminal) and arm swing of the user.
Figure 8B:
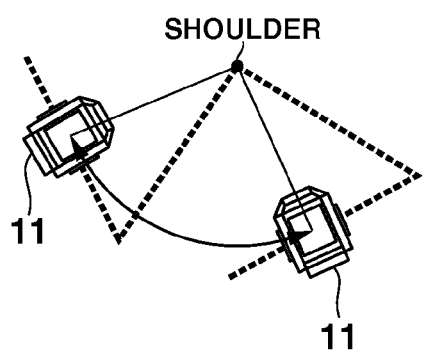
Figure 8C:
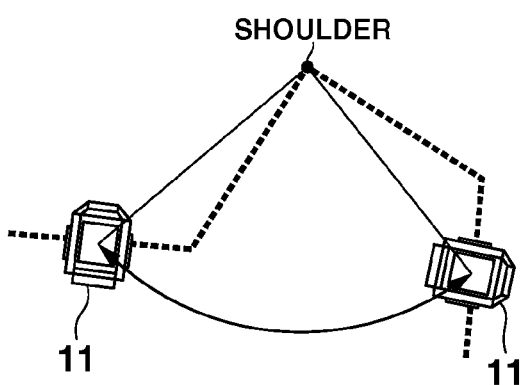

FIGS. 8A, 8B and 8C are views showing relationships between the movement of the wrist terminal 11 and the arm swing. In FIG. 8A, the elbow is bent to a right angle, which will be referred to as a standard. As shown FIG. 8B, when the elbow is bent to an acute angle, a suspending distance will be shorter and the amplitude of the swing of the wrist terminal 11 will be short, and therefore, the acceleration rate will be reduced. When the elbow is bent to the acute angle and the arm is swung at the same cycle as when the elbow is bent to the right angle, the acceleration rate will reduce to a short value and then it will be determined that the elbow has been bent to the acute angle. As shown FIG. 8C, when the elbow is bent to an obtuse angle, the suspending distance will be longer and the amplitude of the swing of the wrist terminal 11 will be large, and therefore, the acceleration rate will increase. When the elbow is bent to the obtuse angle and the arm is swung at the same cycle as when the elbow is bent to the right angle, it will be determined that the elbow has been bent to the obtuse angle.

The controlling unit 120 detects balance of motion in walking or running, such as "the arms are swung well but the leg do not follow the arm swing", from the acceleration components representing the arm swing and the acceleration components representing shocks or timings of the foot landing (step S112). The "acceleration components representing shocks of the foot landing" correspond to a situation in which the wrist terminal 11 is held at the time when the said wrist terminal 11 will receive the shock of foot landing. The acceleration components in the directions of X-, Y- and Z-axes applied to the acceleration sensor (measuring unit 112) from the wrist terminal 11 will change in accordance with a position where the wrist is held at the time when the foot is landed. When the wrist is held substantially at the same position every foot landing, substantially the same acceleration components will be output (acceleration components different depending on the left and right foot). But when the balance in timing between the foot landing and the arm swing is disturbed, the acceleration components in the directions of X-, Y- and Z-axes which are output at the time when foot is landed will change. Therefore, by detecting the acceleration components in the directions of X-, Y- and Z-axes, the balance in timing between foot landing and arm swing can be detected.

For instance, in the acceleration sensor of the wrist terminal 11 worn on the left wrist of the runner as shown in FIG. 4A, the Y-axis is almost always kept vertically. Therefore, the peak value detected when the foot is landed will appear in the acceleration component in the direction of Y-axis (12 o'clock side of the wrist terminal 11). When the arm has been swung forward at the time when the foot is landed, the acceleration component in the direction of X-axis (9 o'clock side of the wrist terminal 11) will increase and when the arm has been swung backward at the time when the foot is landed, the acceleration component in the direction of X-axis (3 o'clock side of the wrist terminal 11) will increase. When Y-axis of the wrist terminal 11 comes to downward, the acceleration component in the direction of X-axis will be approximately zero. When the balance between acceleration components in the directions X- and Y-axes is greatly disturbed, the controlling unit 120 determines that the timing between the arm swing and the foot landing has been disturbed. On the contrary, when substantially the same acceleration components in the directions of X- and Y-axes are output every foot landing, the controlling unit 120 determines that the timing between the arm swing and foot landing is kept right.

Further, when detecting that the above series of processes have been performed "n" times (YES at step S113), the controlling unit 120 sends through the communication unit 122 and IP network 13 data of the generated analysis result to the wrist terminal 11 that has made request for sending back the analysis result (step S114). When the above series of processes have not yet been performed "n" times (NO at step S113), the controlling unit 120 returns to step S104 to perform the process of comparing the walking or running form with the registered exercise forms. When it is determined that the walking or running form substantially coincides with the registered exercise form (YES or = at step S104) and/or when it is determined that the upper half of the body is leaned forward (YES at step S108), similarly the controlling unit 120 sends through the communication unit 122 and IP network 13 the data of the generated analysis result to the wrist terminal 11 which has made request for sending back the analysis result.

Figure 10A:
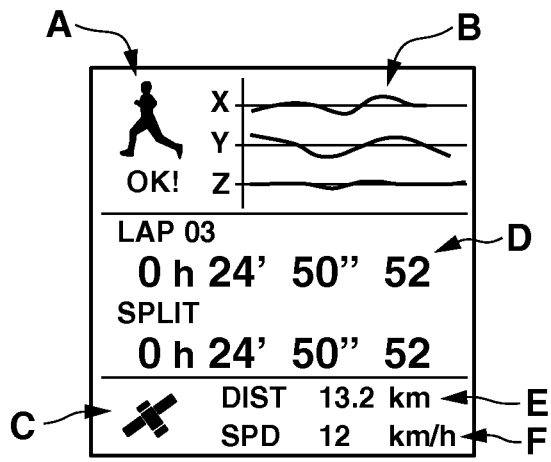
FIGS. 10A, 10B and 10C are views showing samples of indications displayed on a displaying unit of the training supporting apparatus (wrist terminal) in the embodiment of the invention.
Figure 10B:
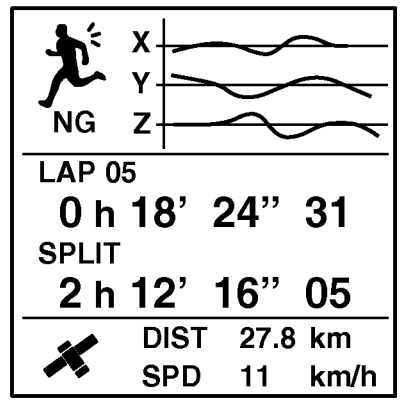
Figure 10C:
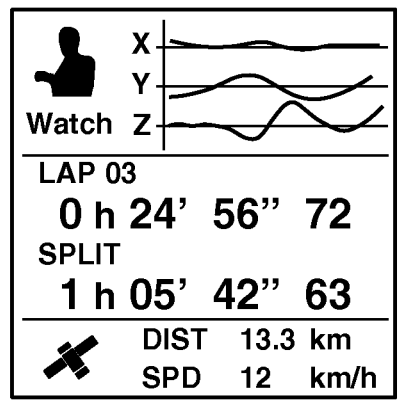

Receiving the data of the analysis result through the communication unit 122 and IP network 13, the wrist terminal 11 displays the data on the displaying unit 115 under control of the controlling unit 110. Samples of the displayed data (images) are shown in FIGS. 10A, 10B and 10C. The contents of the images will be described in detail later.

As shown in the flow chart of FIG. 6, at first the controlling unit 120 judges whether the user is running while looking the wrist terminal 11, and then analyzes the exercise form, in the order of the running posture, the arm swing and the running balance. But the analysis of the exercise form is not restricted to the order of the running posture, the arm swing and the running balance, but can be performed in any order. Since the wrist terminal 11 is worn on one wrist, the tri-axial acceleration components (waveforms) output from the wrist terminal 11 will be different depending on whether the left or the right foot has landed, and therefore it will be appropriate that the acceleration components for two steps (n=2) are used as unit data.

Modified Embodiment

In the training supporting system 1 according to the above described embodiment of the invention, the exercise form analysis is made by the exercise form analyzing server 12. But it is possible to provide a comparatively high-efficient micro-processor on the wrist terminal 11 and to make said wrist terminal 11 make the exercise form analysis, which will be described hereinafter.

In this modified embodiment, the wrist terminal 11 has the same configuration as shown in FIG. 2, but the controlling unit 110 runs a program of a different process. The controlling unit 110 runs the program to perform the following series processes. More specifically, the controlling unit 110 refers to the shock of the foot landing to divide the acceleration components of motion of the user's fitting part, that is, the user's body where the wrist terminal 11 is worn on or fitted to, into the acceleration components at least for one step. Then, the controlling unit 110 compares the divided acceleration components (waveforms) for one step with the previously registered acceleration components (waveforms), and extracts acceleration components of the arm swing at the time of foot landing from the acceleration components successively output from the acceleration sensor (measuring unit 112) when it is determined that the divided acceleration components (waveforms) for one step are different from the previously registered acceleration components (waveforms), whereby the balance in timing between the arm swing and foot landing is analyzed and output.

For the purpose, the controlling unit 110 divides the acceleration components output from the acceleration sensor (measuring unit 112) into the acceleration components at least for one step, on the basis of the acceleration components generated at the times of the foot landings. Further, the controlling unit 110 compares the divided acceleration components (waveforms) with the acceleration components (waveforms) previously registered in the predetermined area of the measuring unit 112. When it is determined that the both acceleration components are different from each other, the controlling unit 110 extracts acceleration components of the arm swing at the time of foot landing from the acceleration components successively output from the acceleration sensor (measuring unit 112), and analyzes and displays on the displaying unit 115 balance in timing between arm swing and foot landing.

Detecting balance between the acceleration components in the directions in X- and Y-axes generated at the time of foot landing, it is also possible for the controlling unit 110 to analyze balance in timing between arm swing and foot landing. Further, it is possible for the controlling unit 110 to sample the acceleration components output from the measuring unit 112 at a given interval, and to delete the sampled acceleration components from the acceleration components to be subjected to the analysis of balance between arm swing and foot landing, wherein said sampled acceleration components include the acceleration component representing substantially zero in the direction of X-axis, the acceleration component in the direction of Y-axis increasing greater than the previous one, and the acceleration components in the directions of Y- and Z-axes having increased in given directions in response to the shock at the time of foot landing. It is also possible for the controlling unit 110 to highlight the result of analyzing balance between arm swing and foot landing while the user is walking or running on an icon representing a pseudo walking or running human.

Figure 9:
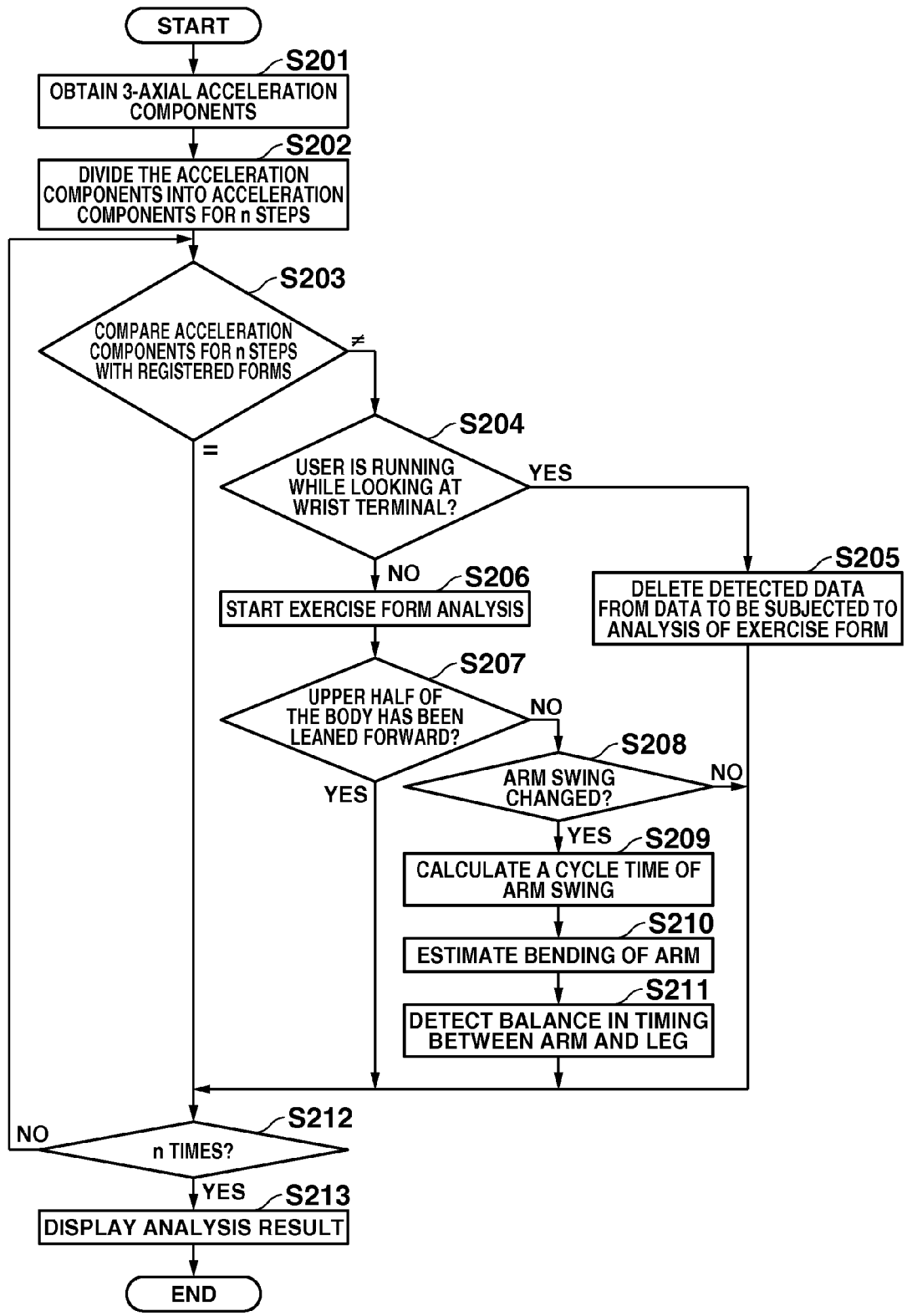
FIG. 9 is a flow chart of operation of the training supporting apparatus (wrist terminal) according to the modified embodiment of the invention.

FIG. 9 is a flow chart of operation of the wrist terminal 11 in the modified embodiment of the invention.

When the operation unit 114 is operated by the user, the measuring unit 112 of the wrist terminal 11 makes the acceleration sensor start detecting acceleration components of motion of the fitting part, that is, the user's body where the wrist terminal 11 is worn on or fitted to, in the three directions along the X-, Y-, and Z-axes, and the controlling unit 110 obtains the tri-axial acceleration components (step S201). The controlling unit 110 divides the tri-axial acceleration components into data components of n steps (one step or tow steps) (step S202). The controlling unit 110 detects the peak values appearing in the acceleration components (waveform) to divide the same components. This is because the greatest shocks are given to the wrist terminal 11 every foot landings while the user is walking or running.

Dividing the tri-axial acceleration components output from the measuring unit 112 into the acceleration components of n steps (step S202), the controlling unit 110 compares the divided acceleration components with the acceleration components of the normally walking or running forms of n steps previously registered in a predetermined area of the storing unit 111 (step S203). When the user breaks his/her normal walking or running form, that is, when it is determined that the walking or running form does not coincide with the registered exercise form (NO or ≠ at step S203), the controlling unit 110 will perform the following operation.

When the user breaks the normal form, it is estimated that the user is running, while looking at the wrist terminal 11. When the user has taken motion of looking at the wrist terminal 11 (YES at step S204), the wrist terminal 11 is brought before the user's face, and it is clear that the user does not take the right exercise form. Since the user is looking at the wrist terminal 11, when the measuring unit 112 has detected that the user is looking at the wrist terminal 11, the detected data is deleted from data to be subjected to the exercise form analysis (step S205). When it is determined that the user is walking or running without looking at the wrist terminal 11 (NO at step S204), the controlling unit 110 starts the exercise form analysis (step S206).

When the running form is analyzed, the controlling unit 110 judges whether the runner has leaned the upper half of the body forward (step S207). When the upper half of the body has been leaned forward, the position of the wrist terminal 11 is changed and the way of foot landing also changes accordingly. Therefore, since the acceleration rates (waveforms) in the directions of X-, Y- and Z-axes transferred to the tri-axial built-in acceleration sensor of the measuring unit 112 will be different from the waveform obtained while the user is running in the normal posture, it will be easily determined (at step S108) whether the runner has leaned the upper half of the body forward. When the controlling unit 120 has determined that the upper half of the body is not leaned forward (NO at step S207), the controlling unit 120 judges whether the user has changed the arm swing (step S208).

When the user has changed the arm swing (YES at step S208), for example, when the user's arm is swung sideways not back and forward, the waveform of either one of the acceleration rates in the directions of X-, Y- and Z-axes sent to the built-in acceleration sensor (measuring unit 112) will change, and therefore it can easily be determined that the arm swing has changed. In the present embodiment, since the direction perpendicular to the glass surface 21 and the rear cover 22 of the wrist terminal 11 worn on the user's wrist is defined as Z-axis, if it is assumed that the wrist terminal 11 is worn on the back of the wrist and that the arm is straightly swung back and forward, the acceleration components are generated substantially in the directions of X-, and Y-axes but little acceleration component is detected in the direction of Z-axis. If the arm is swung sideways, the acceleration component will increase in the direction of Z-axis, which the controlling unit 110 will detect.

Then, extracting a back and forward motion of the arm swing from the acceleration components in the directions of X-, Y- and Z-axes output from the tri-axial acceleration sensor (measuring unit 112), the controlling unit 110 calculates a cycle time of the arm swing (step S209) and estimates bending of the arm (arm-swing rate and arm bending angle) (step S210). In particular, the arm swing plays an important roll to produce a rhythm of walking or running. Since the cycle time of the arm swing corresponds to a repetition of the acceleration components in the directions of X- and Y-axes, the cycle time of the arm swing can be obtained by detecting a timing at which substantially the same waveform repeatedly appears. When the arm is bent too much, the wrist terminal 11 will be swung with in a short range, and on the contrary, when the arm is not bent too much but rather kept straight, the wrist terminal 11 will be swung greatly. In this way, the amplitude of the arm swing can be calculated by analyzing the cycle time of the arm swing and the acceleration components of motion of the arm swing, whereby how much the arm is bent can be estimated.

The controlling unit 110 detects balance in timing between leg and arm from the timing of acceleration components indicating the arm swing and the timing of the acceleration components indicating shock of foot landings (step S211). When the foot is landed, the peak value of the acceleration component will appear in the direction of Y-axis (12 o'clock side of the wrist terminal 11). When the arm has been swung forward at the time when the foot is landed, the acceleration component in the direction of X-axis (9 o'clock side of the wrist terminal 11) will increase and when the arm has been swung backward at the time when the foot is landed, the acceleration component in the direction of X-axis (3 o'clock side of the wrist terminal 11) will increase. When Y-axis of the wrist terminal 11 comes to the downward, the acceleration component in the direction of X-axis will be approximately zero. When the balance between acceleration components in the directions X- and Y-axes is greatly disturbed, the controlling unit 120 determines that the timing between the arm swing and the foot landing has been disturbed. On the contrary, when substantially the same acceleration components in the directions of X- and Y-axes are output every foot landing, the controlling unit 120 determines that the timing between the arm swing and foot landing is kept right.

Further, when detecting that the above series of processes have been performed "n" times (YES at step S212), the controlling unit 110 sends data of the generated analysis result to the displaying unit 115. When the above series of processes have not yet been performed "n" times (NO at step S212), the controlling unit 120 returns to step S203 to perform the process of comparing the walking or running form with the registered exercise form. When it is determined that the walking or running form substantially coincides with the registered exercise form (= or YES at step S203) and/or when it is determined that the upper half of the body is leaned forward (YES at step S207), similarly the controlling unit 110 sends data of the generated analysis result to the displaying unit 115.

The displaying unit 115 displays indications shown in FIGS. 10A, 10B and 10C under control of the controlling unit 110. The indication of FIG. 10A represents the normal running posture (OK posture) which coincides with the registered exercise form. The indication of FIG. 10B represents a posture (NG posture) different from the normal running posture (registered exercise form). The indication of FIG. 10C represents a posture of the user who is running while looking at or watching the wrist terminal 11.

Each of the indications shown in FIGS. 10A, 10B and 10C is divided into plural displaying areas A, B, C, and D. In the displaying area "A", a running indicator or an icon representing a running posture is displayed. In the displaying area "B", the acceleration rates are indicated in the vertical axis and waveforms of the acceleration components are indicated along the horizontal X-, Y- and Z-axes with time scale added. In the displaying area "C", a position calculated by GPS, a calculated distance, velocity data, and GPS receipt indicator are displayed. In the displaying area "D", measured times are indicated, such as a lap time on the top and a split time at the bottom.

In FIG. 10B, the part of the user's body deemed to be "NG" is highlighted in the running indicator of the displaying area "A". It is determined that the arm swing is not good and the arm is blinking. Looking at the indication, the runner can easily understand whether his/her own running form during running is good or not. In other words, the indications of FIGS. 10A, 10B and 10C give the user a guidance and the user can use the indications as an advice. To avoid requesting the user to look at the indication frequently as possible, it is possible to make the buzzer sounding unit 117 produce an aural message to tell the guidance in place of the indication on the displaying unit 115.

In the training supporting system 1 according to the embodiment, the wrist terminal 11 used by the user is small and light. Therefore, when the user wears such wrist terminal 11 on his/her wrist and walks or runs, the user is released from trouble of wearing a smartphone on his/her waist and walking or running. The exercise form analyzing server 12 is used to analyze the running form in which arm swing specially plays an important roll in running, and the wrist terminal 11 receives the analysis result through communication with the form analyzing server 12, whereby calculation load on the wrist terminal 11 will be light. Using the form analyzing server 12 and the wrist terminal 11, an advanced exercise form analysis can be made such as analyzing balance between arm swing and foot landing while the user is walking or running.

It is possible to use the wrist terminal 11 to make a part of the exercise from analysis in place of the form analyzing server 12. In this case, only the wrist terminal 11 is used to make the exercise form analysis, whereby motion data of a trace of arm swing while the user is running can be obtained without employing an image processing technology such as a motion capture. It is also possible to make an advanced exercise form analysis such as analyzing balance between arm swing and foot landing while the user is walking or running. A training supporting apparatus and system, a form analyzing apparatus and method, and an exercise form analyzing program, for making the exercise form analysis efficiently and enhanced exercise form analysis are provided.

The training supporting system 1 according to the embodiments of the invention which is used by the user while he/she is walking and/or running has been described, but this training supporting system can be used in the any fields of sports such as cycling, triathlons, and other exercises.

Although specific embodiments of the invention have been described in the foregoing detailed description, it will be understood that the invention is not limited to the particular embodiments described herein, but modifications and rearrangements may be made to the disclosed embodiments while remaining within the scope of the invention as defined by the following claims. It is intended to include all such modifications and rearrangements in the following claims and their equivalents.—

DESCRIPTION OF REFERENCE NUMERALS AND SIGNALS

1: Training supporting system
11: Wrist terminal (Training supporting apparatus)
12: Form analyzing server (Form analyzing apparatus)
13: IP network (communication network)
21: Glass surface
22: Rear cover
23: Wrist band
110: Controlling unit
111: Storing unit
112: Measuring unit
113: Communication unit
114: Operation unit
115: Displaying unit
116: GPS receiving unit
117: Buzzer sounding unit
118: Power source unit
120: Controlling unit
121: Storing unit
122: Communication unit
123: Operation unit
124: Displaying unit
125: System bus

What is claimed is:

1. A training supporting apparatus used to analyze an exercise form while a user is walking or running, the apparatus comprising:
    a sensor which is worn by a part of an arm of the user and measures acceleration components of the part of the arm of the user at least in three directions along X-, Y- and Z-axes, while the user is walking or running; and
    a processor which outputs an analysis result including a balance between arm swing and foot landing of the user analyzed based on information of the acceleration components measured by the sensor, wherein the processor detects a change in a balance between the acceleration component in the direction of the X-axis and the acceleration component in the direction of the Y-axis at a time of the foot landing, thereby analyzing a timing balance between the arm swing and the foot landing of the user.

2. An exercise form analyzing apparatus which is connected to a training supporting apparatus through a communication network, wherein the training supporting apparatus is worn by a part of an arm of a user and measures acceleration components of the part of the arm of the user at least in three directions along X-, Y- and Z-axes, while the user is walking or running, the exercise form analyzing apparatus comprising:

a processor which analyzes an exercise form of the user including a balance between arm swing and foot landing, based on the acceleration components received from the training supporting apparatus through the communication network, and sends an analysis result of the exercise form of the user to the training supporting apparatus through the communication network, wherein the processor detects a change in a balance between the acceleration component in the direction of the X-axis and the acceleration component in the direction of the Y-axis at a time of the foot landing, thereby analyzing a timing balance between the arm swing and the foot landing of the user.

3. The exercise form analyzing apparatus according to claim 2, wherein the processor samples at prescribed intervals the acceleration components received from the training supporting apparatus through the communication network to obtain plural pieces of sampled data for analyzing the balance, and excludes data from the plural pieces of sampled data for analyzing the timing balance, wherein the data has the acceleration component in the direction of the X-axis which is approximately zero, the acceleration component in the direction of the Y-axis which has increased greater than previously sampled acceleration component and the acceleration components in the directions of the Y-, and Z-axes which have increased in predetermined directions at a shock of foot landing.

4. A non-transitory computer-readable storage medium with an executable program stored thereon, the program being used in a training supporting apparatus worn on a part of an arm of a user and, when installed on a computer, causing the computer to perform procedures including:

a procedure of measuring acceleration components of the part of the arm of the user at least in three directions along X-, Y- and Z-axes, while the user is walking or running; and a procedure of outputting an analysis result which includes a balance between arm swing and foot landing of the user analyzed based on information of the measured acceleration components, wherein in the procedure of outputting an analysis result, a change is detected in a balance between the acceleration component in the direction of the X-axis and the acceleration component in the direction of the Y-axis at a time of the foot landing, whereby a timing balance between the arm swing and the foot landing of the user is analyzed.

5. A non-transitory computer-readable storage medium with an executable program stored thereon, the program being used in an exercise form analyzing apparatus connected to a training supporting apparatus through a communication network, wherein the training supporting apparatus is worn on a part of an arm of a user and is provided with a computer and a sensor for measuring acceleration components of the part of the arm of the user at least in three directions along X-, Y- and Z-axes, while the user is walking or running, the program, when installed on a computer, causing the computer to perform procedures including:

a procedure of obtaining the acceleration components from the training supporting apparatus through the communication network;

a procedure of analyzing an exercise form of the user including a balance between arm swing and foot landing, based on the obtained acceleration components; and a procedure of sending an analysis result of the exercise form of the user to the training supporting apparatus through the communication network, wherein in the procedure of analyzing an exercise form, a change is detected in a balance between the acceleration component in the direction of the X-axis and the acceleration component in the direction of the Y-axis at a time of the foot landing, whereby a timing balance between the arm swing and the foot landing of the user is analyzed.

6. A training supporting apparatus comprising:

a sensor which is worn on a part of an arm of a user and measures acceleration components of the part of the arm of the user at least in three directions along X-, Y- and Z-axes, while the user is walking or running; and a processor which (a) divides the acceleration components output from the sensor into acceleration components at least for one step with the acceleration component at foot landing as a base point, (b) compares waveforms of the divided acceleration components with previously registered waveforms of acceleration components, (c) extracts acceleration components of arm swing at the time of foot landing from the acceleration components successively output from the sensor, when it is determined the waveforms do not coincide with each other, thereby analyzing a timing balance between arm swing and foot landing while the user is walking or running, and (d) outputs the analyzed timing balance between the arm swing and foot landing of the user.

7. The training supporting apparatus according to claim 6, wherein the processor divides the acceleration components output from the sensor into acceleration components at least for one step with the acceleration components at foot landing as the base points.

8. The training supporting apparatus according to claim 6, wherein the processor compares waveforms of the divided acceleration components with previously registered waveforms of acceleration components, and extracts acceleration components of arm swing at the time of foot landing from the acceleration components successively output from the sensor, when it is determined the both waveforms do not coincide with each other, thereby analyzing a timing balance between arm swing and foot landing while the user is walking or running, and outputs the analyzed timing balance between the arm swing and foot landing of the user.

9. The training supporting apparatus according to claim 6, wherein the processor detects a change in a balance between the acceleration component in the direction of the X-axis and the acceleration component in the direction of the Y-axis at a time of the foot landing, thereby analyzing a timing balance between the arm swing and the foot landing of the user.

10. The training supporting apparatus according to claim 6, wherein the processor samples at prescribed intervals the acceleration components output from the sensor to obtain plural pieces of sampled data for analyzing the balance, and excludes data from the plural pieces of sampled data for analyzing the timing balance, wherein the data has the acceleration component in the direction of the X-axis which is approximately zero, the acceleration component in the direction of the Y-axis which has increased greater than previously sampled acceleration component and the acceleration components in the directions of the Y-, and Z-axes which have increased in predetermined directions at a shock of foot landing.

11. The training supporting apparatus according to claim 6, further comprising:
   a display;
   wherein the processor displays a guidance screen on the display in accordance with the analyzed timing balance between the arm swing and foot landing while the user is walking or running.

12. The training supporting apparatus according to claim 6, further comprising:
   a display;
   wherein the processor highlights on the display an icon simulating a person walking or running, which icon represents the analyzed timing balance between the arm swing and foot landing while the user is walking or running.

13. A non-transitory computer-readable storage medium with an executable program stored thereon, the program being used in a training supporting apparatus, wherein the training supporting apparatus is worn on a part of the arm of a user and measures acceleration components of the part of the arm of the user at least in three directions along X-, Y- and Z-axes, while the user is walking or running, the program, when installed on a computer, causing the computer to perform procedures including:
   dividing the acceleration components of the part of the arm of the user into acceleration components at least for one step with the acceleration component at foot landing as a base point;
   comparing waveforms of the divided acceleration components with previously registered waveforms of acceleration components; and
   extracting acceleration components of arm swing at the time of foot landing from the successively output acceleration components, when it is determined the waveforms do not coincide with each other, thereby analyzing a timing balance between arm swing and foot landing while the user is walking or running, and outputting the analyzed timing balance between the arm swing and foot landing of the user.

* * * * *